United States Patent
Hokari

(10) Patent No.: US 9,642,553 B2
(45) Date of Patent: May 9, 2017

(54) MAGNETIC FIELD MEASURING APPARATUS AND CELL ARRAY

(71) Applicant: Seiko Epson Corporation, Tokyo (JP)

(72) Inventor: Ryuji Hokari, Ota (JP)

(73) Assignee: Seiko Epson Corporation (JP)

( * ) Notice: Subject to any disclaimer, the term of this patent is extended or adjusted under 35 U.S.C. 154(b) by 282 days.

(21) Appl. No.: 13/712,139

(22) Filed: Dec. 12, 2012

(65) Prior Publication Data

US 2013/0150702 A1    Jun. 13, 2013

(30) Foreign Application Priority Data

Dec. 13, 2011  (JP) ................. 2011-272345

(51) Int. Cl.
*A61B 5/05* (2006.01)
*A61B 5/00* (2006.01)
*A61B 5/04* (2006.01)

(52) U.S. Cl.
CPC .............. *A61B 5/05* (2013.01); *A61B 5/0044* (2013.01); *A61B 5/04007* (2013.01); *A61B 2562/0223* (2013.01); *A61B 2562/046* (2013.01)

(58) Field of Classification Search
None
See application file for complete search history.

(56) References Cited

U.S. PATENT DOCUMENTS

| | | | |
|---|---|---|---|
| 6,690,162 B1 * | 2/2004 | Schopohl et al. ............ | 324/248 |
| 2005/0148844 A1 | 7/2005 | Ogata et al. | |
| 2006/0079751 A1 | 4/2006 | Kandori et al. | |
| 2008/0084204 A1 | 4/2008 | Seki et al. | |
| 2009/0289629 A1 * | 11/2009 | Tuchman ................. | 324/304 |
| 2010/0327862 A1 | 12/2010 | Nagasaka | |
| 2011/0101974 A1 | 5/2011 | Nagasaka | |
| 2015/0115948 A1 | 4/2015 | Nagasaka | |

FOREIGN PATENT DOCUMENTS

| | | |
|---|---|---|
| JP | 07-077564 | 3/1995 |
| JP | 11-253412 | 9/1999 |
| JP | 2000-041965 | 2/2000 |
| JP | 2000-051169 A | 2/2000 |
| JP | 2005-080951 | 3/2005 |
| JP | 2006-094984 | 4/2006 |
| JP | 2008-086675 | 4/2008 |
| JP | 2011-007567 A | 1/2011 |
| JP | 2011-510328 A | 3/2011 |
| JP | 2011-095106 A | 5/2011 |
| JP | 2011-232277 A | 11/2011 |
| WO | WO-2010-082932 A1 | 7/2010 |

* cited by examiner

*Primary Examiner* — Joseph M Santos Rodriguez
(74) *Attorney, Agent, or Firm* — Harness, Dickey & Pierce, P.L.C.

(57) ABSTRACT

A magnetic field measuring apparatus includes a cell array which includes plural cells different in size of detection surface through which a magnetic flux passes when the cells are arranged in a magnetic field of a measurement object, a medium which is enclosed inside each of the plural cells and rotates a light polarization plane according to an intensity of the magnetic field, an irradiator to irradiate a light to the detection surface of each of the cells, and a detector to detect a rotation angle of a polarization plane of the light passing through each of the cells.

6 Claims, 7 Drawing Sheets

MAGNETIC FIELD MEASURING APPARATUS AND CELL ARRAY

BACKGROUND

1. Technical Field

The present invention relates to a technique to measure a magnetic field generated from a living body.

2. Related Art

As a sensor to measure a very weak magnetic field generated from a heart or a brain, a SQUID (Superconducting Quantum Interference Device) sensor is known (see JP-A-11-253412, JP-A-2000-41965, JP-A-2008-86675, JP-A-7-77564, JP-A-2006-754403, JP-A-2006-94984 and JP-A-2005-80951).

In general, when a magnetic field is measured by using a magnetic sensor, in order to raise spatial resolution, it is necessary to miniaturize the magnetic sensor and to increase the number of magnetic sensors per unit area. However, if the magnetic sensor is miniaturized, the sensitivity becomes low, and accordingly, a very weak magnetic field can not be measured.

SUMMARY

An advantage of some aspects of the invention is to raise spatial resolution in magnetic field measurement and to reduce the measurement lower limit.

An aspect of the invention is directed to a magnetic field measuring apparatus including a cell array which includes plural cells different in size of detection surface through which a magnetic flux passes when the cells are arranged in a magnetic field of a measurement object, and in which the plural cells are arranged to make the number thereof per unit area larger than a threshold, a medium which is enclosed inside each of the plural cells and rotates a light polarization plane according to an intensity of the magnetic field, an irradiator to irradiate a light to the detection surface of each of the cells, and a detector to detect a rotation angle of a polarization plane of the light passing through each of the cells. According to this structure, the spatial resolution in the magnetic field measurement is raised, and the measurement lower limit can be reduced.

The plural cells may be arranged to cover a generation source of the magnetic field of the measurement object from plural directions. According to this structure, the magnetic fields of plural axial direction components can be measured.

The generation source may be a heart of a human, and a first cell included in the plural cells may be arranged on a front surface side of the human. According to this structure, the spatial resolution when the magnetic field is measured from the front surface of the human can be raised.

A second cell having the detection surface larger than the first cell among the plural cells may be arranged on a side surface side or a back surface side of the human. According to this structure, the measurement lower limit when the magnetic field is measured from the side surface or the back surface of the human can be reduced.

The first cell may be arranged in an area within a specified range from the heart on the side surface side or the back surface side of the human. According to this structure, even when the magnetic field is measured from the side surface or the back surface of the human, the spatial resolution can be raised in the area within the specified range from the heart.

The plural cells may be arranged to cover the generation source of the magnetic field of the measurement object from a single direction, a first cell included in the plural cells is arranged in an area within a specified range from the generation source, and a second cell having a detection surface larger than the first cell is arranged in other area. According to this structure, the spatial resolution can be raised when the magnetic field is measured in the area within the specified range from the measurement object, and the measurement limit can be reduced when the magnetic field is measured in the other area.

Another aspect of the invention is directed to a cell array including plural cells different in size of detection surface through which a magnetic flux passes when the cells are arranged in a magnetic field of a measurement object, and a medium which is enclosed inside each of the plural cells and rotates a light polarization plane according to an intensity of the magnetic field, and the plural cells are arranged to make the number thereof per unit area larger than a threshold. According to this structure, when the magnetic field is measured by using the cell array, the spatial resolution in the magnetic field measurement is raised, and the measurement lower limit can be reduced.

BRIEF DESCRIPTION OF THE DRAWINGS

The invention will be described with reference to the accompanying drawings, wherein like numbers reference like elements.

DESCRIPTION OF EXEMPLARY EMBODIMENTS

1. Embodiments

Figure 1:
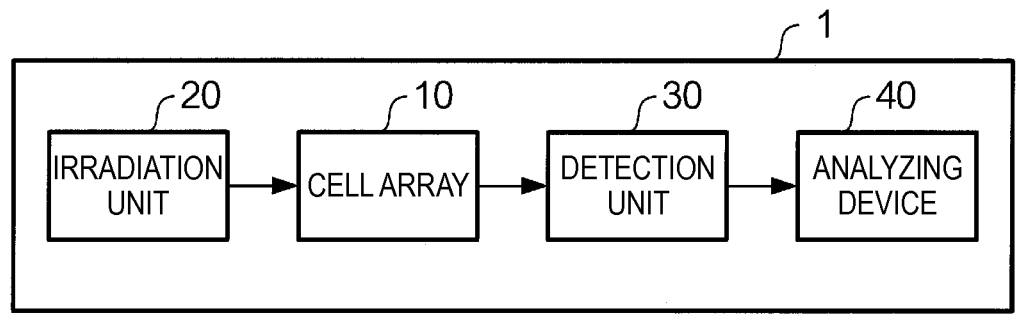
FIG. 1 is a block diagram showing a structure of a magnetic field measuring apparatus.

FIG. 1 is a block diagram showing a structure of a magnetic field measuring apparatus 1 of an embodiment. The magnetic field measuring apparatus 1 is, for example, an optical pumping type magnetic sensor. The magnetic field measuring apparatus 1 is used in, for example, a magnetocardiograph to measure a magnetic field (magnetocardiogram) generated from a heart.

The magnetic field measuring apparatus 1 includes a cell array 10, an irradiation unit 20 (an example of an irradiator), a detection unit 30 (an example of a detector), and an analyzing device 40. The cell array 10 includes plural cells 11. The cell 11 is formed of a material having light transparency, such as quartz or glass. An alkali metal atom 15 (for example, cesium) is enclosed inside the cell 11. The alkali metal atom 15 is a medium to rotate a light polarization plane according to the intensity of a magnetic field. The cell 11 has, for example, a cubic shape. Surfaces constituting the cell 11 includes a detection surface 12 through which a magnetic flux passes when the cell 11 is arranged in the magnetic field of a measurement object.

The irradiation unit 20 includes a light source, a polarizing part and a light distributor. The light source emits a laser light. The polarizing part polarizes the laser light emitted from the light source, and generates a detection light L1 having a linearly polarized component. The light distributor branches the detection light L1 generated by the polarizing part into lights the number of which is equal to the number of the cells 11 included in the cell array 10. The detection light L1 branched into plural lights by the light distributor is guided by, for example, an optical fiber, and is irradiated to each of the cells 11 included in the cell array 10. The detection light L1 irradiated to each of the cells 11 passes through the cell 11. At this time, the polarization plane of the detection light L1 is rotated by the alkali metal atom 15 enclosed inside the cell 11 (Faraday effect).

The detection unit 30 includes detectors 31 the number of which is equal to the number of the cells 11 included in the cell array 10. The detector 31 detects a rotation angle of the polarization plane of the light passing through the corresponding cell 11, and outputs a signal corresponding to the detected rotation angle. The analyzing device 40 includes a CPU (Central Processing Unit) and a memory. Information indicating the correspondence relation between the intensity of the magnetic field and the rotation angle of the polarization plane of the detection light L1 is previously stored in the memory. The CPU uses the signal outputted from the detection unit 30 and calculates the intensity of the magnetic field based on the information stored in the memory. In this way, the magnetic field is measured.

Figure 2:
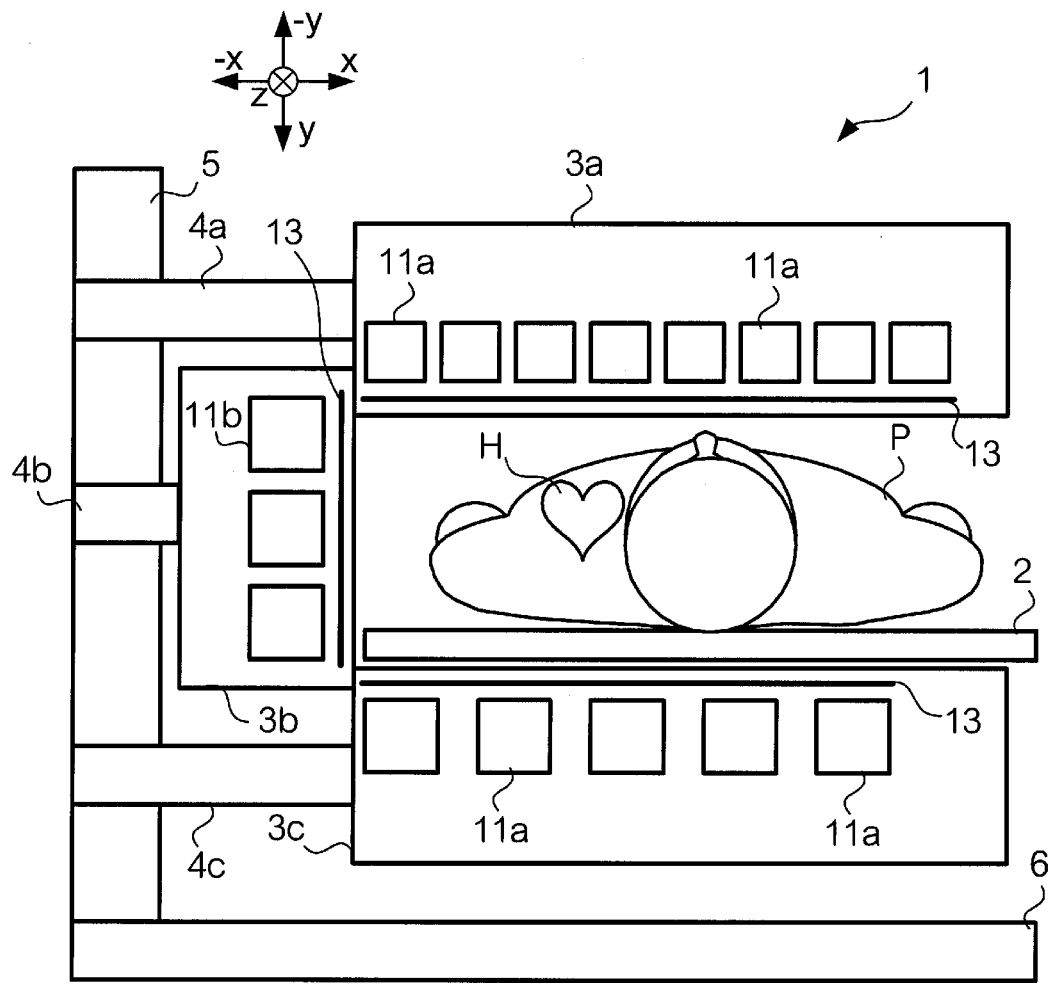
FIG. 2 is a view showing the whole structure of the magnetic field measuring apparatus.

FIG. 2 is a view showing the whole structure of the magnetic field measuring apparatus 1. Incidentally, in this drawing, the illustration of the irradiation unit 20, the detection unit 30 and the analyzing device 40 is omitted. The magnetic field measuring apparatus 1 includes a bed 2 on which a subject P (human) is made to lie. When the magnetocardiogram of the subject P is measured, the subject P is generally made to lie on his or her back on the bed 2.

The plural cells 11 included in the cell array 10 are arranged to cover the heart H (an example of a generation source of a magnetic field of a measurement object) from three directions of the front surface, the left surface and the back surface of the subject P. Incidentally, here, the word "cover" does not mean that the adjacent cells 11 are arranged without any gap so that the heart H is completely concealed. A gap may exist between the adjacent cells 11. Specifically, the plural cells 11 are arranged on the front surface side, the left side surface side and the back surface side of the subject P so that distances from the subject P become minimum distances. The front surface side means an area positioned in the −y-axis direction when viewed from the subject P. The left side surface side means an area positioned in the −x-axis direction when viewed from the subject P. The back surface side means an area positioned in the y-axis direction when viewed from the subject P.

The magnetic field measuring apparatus 1 includes a housing 3a to contain the cells 11 arranged on the front surface side of the subject P, a housing 3b to contain the cells 11 arranged on the left side surface side of the subject P, and a housing 3c to contain the cells 11 arranged on the back surface side of the subject P. In the housings 3a, 3b and 3c, the cells 11 are supported by not-shown support parts fixed to the housings. Besides, a mirror 13 is provided between each of the cells 11 and the subject P. The housings 3a, 3b, 3c are respectively supported by arms 4a, 4b and 4c connected to a strut 5. The strut 5 is fixed by a base part 6.

Figure 3:
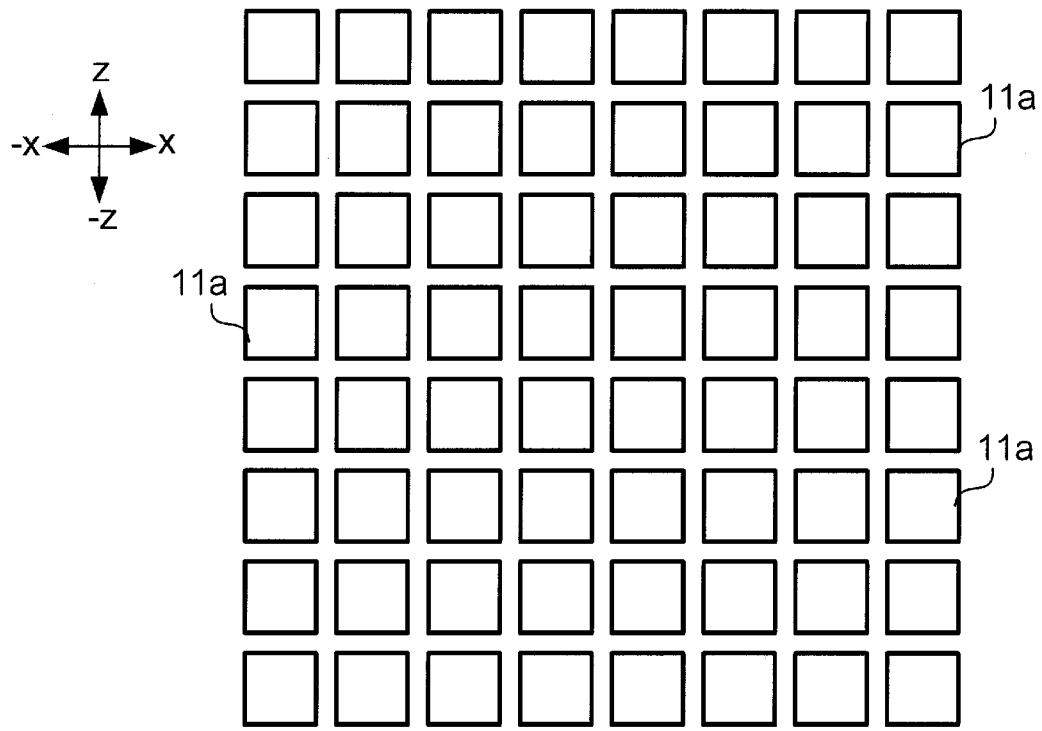
FIG. 3 is a view in which cells arranged on the front surface side of a subject are seen in a y-axis direction of FIG. 2.

FIG. 3 is a view in which the cells 11 arranged on the front surface side of the subject P are seen from the y-axis direction shown in FIG. 2. First cells 11a are arranged in a matrix of 8 rows by 8 columns on the front surface side of the subject P. The first cells 11a are smaller than aftermentioned second cells 11b arranged on the left side surface side or the back surface side of the subject P. The size of the detection surface 12 of the first cell 11a is previously set according to the intensity of a magnetic field on the front surface side of the subject P. For example, the detection surface 12 of the first cell 11a is set to a minimum size within a range in which a measurement lower limit not lower than the intensity of the magnetic field on the front surface side of the subject P is obtained. The measurement lower limit means the minimum intensity of a magnetic field that can be measured.

Figure 4:
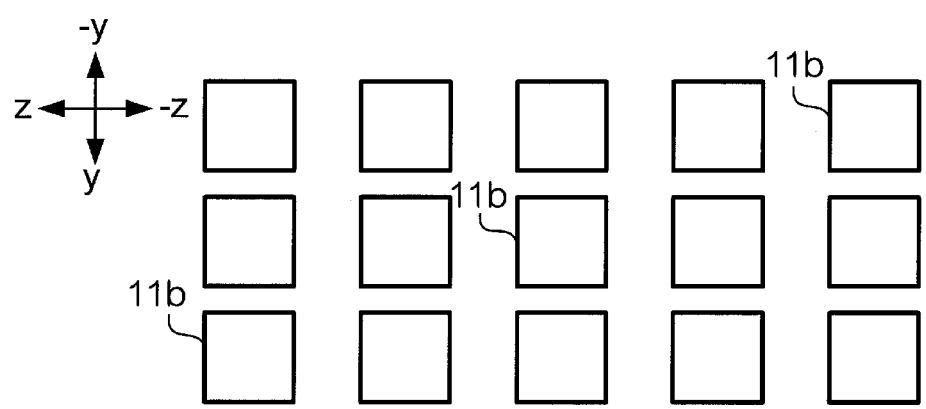
FIG. 4 is a view in which cells arranged on the left side surface side of the subject are seen in an x-axis direction of FIG. 2.

FIG. 4 is a view in which the second cells 11b arranged on the left side surface side of the subject P are seen from the x-axis direction shown in FIG. 2. The second cells 11b are arranged in a matrix of 3 rows by 5 columns on the left side surface side of the subject P. The second cell 11b is larger than the first cell 11a arranged on the front surface side of the subject P. Incidentally, the second cell 11b is larger than the first cell 11 not only in the whole size but also in the size of the detection surface 12.

Figure 5:
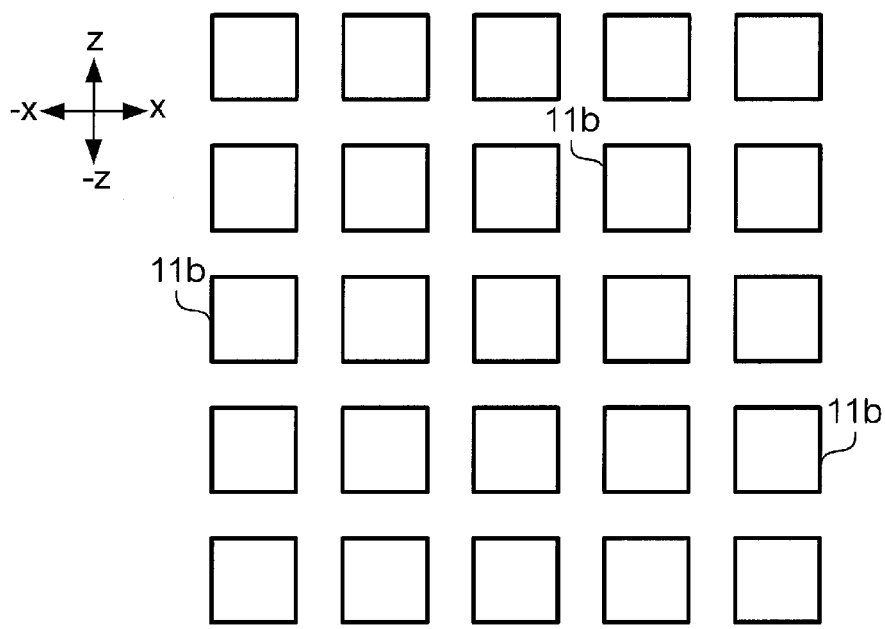
FIG. 5 is a view in which cells arranged on the back surface side of the subject are seen in a −y-axis direction of FIG. 2.

FIG. 5 is a view in which the second cells 11b arranged on the back surface side of the subject P are seen from the −y-axis direction shown in FIG. 2. The second cells 11b are arranged in a matrix of 5 rows by 5 columns on the back surface side of the subject P. The second cell 11b is larger than the first cell 11a arranged on the front surface side of the subject P. Incidentally, the second cell 11b is larger than the first cell 11a not only in the whole size but also in the size of the detection surface 12.

Since the first cell 11a is smaller than the second cell 11b, the first cells are arranged so that the number thereof per unit area becomes larger. For example, although FIG. 3 and FIG. 5 show the cells 11 arranged in the same area, the number of the second cells 11b shown in FIG. 5 is 5×5=25, while the number of the first cells 11a shown in FIG. 3 is 8×8=64. As stated above, the first cells 11a are arranged so that the number thereof per unit area is larger than the number (an example of a threshold) of the second cells 11b per unit area.

Figure 6:
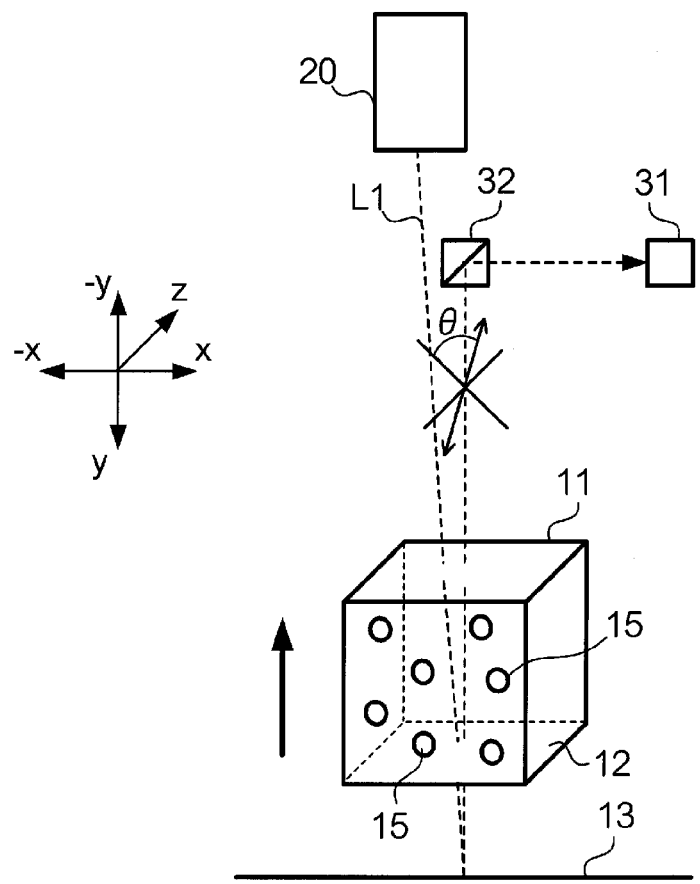
FIG. 6 is a view for explaining the principle of measuring a magnetic field from the front surface of the subject.

FIG. 6 is a view for explaining the principle of measuring a magnetic field from the front surface of the subject P. In FIG. 6, directions are indicated using a three-dimensional coordinate system (left-hand system). Incidentally, since the principle of measuring a magnetic field is the same in both cases of using the first cells 11a and the second cells 11b, here, these cells are generally called "cells 11". Besides, in this drawing, for facilitating the explanation, only one of the plural cells 11 arranged on the front surface side of the subject P is shown.

The cell 11 arranged on the front surface side of the subject P includes the detection surface 12 parallel to an xz plane. The irradiation unit 20 irradiates the detection light L1 to a surface of the cell 11 opposite to the detection surface 12. The detection light L1 irradiated from the irradiation unit 20 is incident on this surface and passes through the cell 11. The detection light L1 passing through the cell 11 is reflected by the mirror 13, is incident on the detection surface 12 of the cell 11, and passes through the cell 11 in the −y-axis direction. At this time, the polarization plane of the detection light L1 is rotated by the alkali metal atom 15 in the cell 11 by a rotation angle θ according to the intensity of the magnetic field in the −y-axis direction. The detection light L1 passing through the cell 11 is guided by a mirror 32 to the detector 31. When receiving the detection light L1, the detector 31 detects the rotation angle θ of the polarization plane of the detection light L1. The rotation angle θ has a value corresponding to the intensity of the magnetic field in the −y-axis direction in the cell 11. Accordingly, the magnetic field in the −y-axis direction in the cell 11 can be measured by detecting the rotation angle θ.

Figure 7:
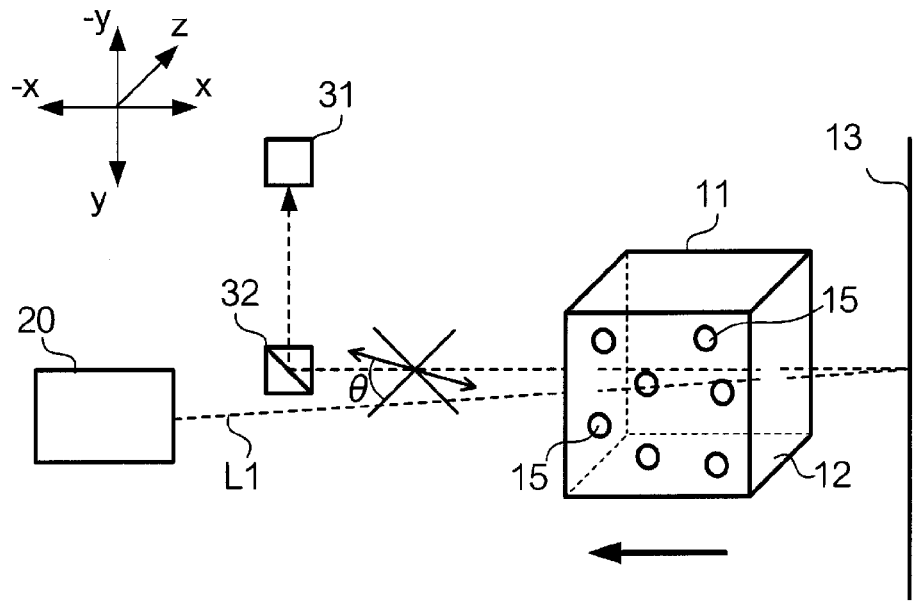
FIG. 7 is a view for explaining the principle of measuring a magnetic field from the left side surface of the subject.

FIG. 7 is a view for explaining the principle of measuring a magnetic field from the left side surface side of the subject P. In FIG. 7, directions are indicated by using the three-dimensional coordinate system (left-hand system). Besides, in this drawing, for facilitating the explanation, only one of the plural cells 11 arranged on the left side surface side of the subject P is shown.

The cell 11 arranged on the left side surface side of the subject P includes the detection surface 12 parallel to a yz plane. The irradiation unit 20 irradiates the detection light L1 to a surface of the cell 11 opposite to the detection surface 12. The detection light L1 irradiated from the irradiation unit 20 is incident on this surface and passes through the cell 11. The detection light L1 passing through the cell 11 is reflected by the mirror 13, is incident on the detection surface 12 of the cell 11, and passes through the cell 11 in the −x-axis direction. At this time, the polarization plane of the detection light L1 is rotated by the alkali metal atom 15 in the cell 11 by a rotation angle θ according to the intensity of the magnetic field in the −x-axis direction. The detection light L1 passing through the cell 11 is guided to the detector 31 by a mirror 32. When receiving the detection light L1, the detector 31 detects the rotation angle θ of the polarization plane of the detection light L1. The rotation angle θ has a value corresponding to the intensity of the magnetic field in the −x-axis direction in the cell 11. Accordingly, the magnetic field in the −x-axis direction in the cell 11 can be measured by the detecting the rotation angle θ.

Figure 8:
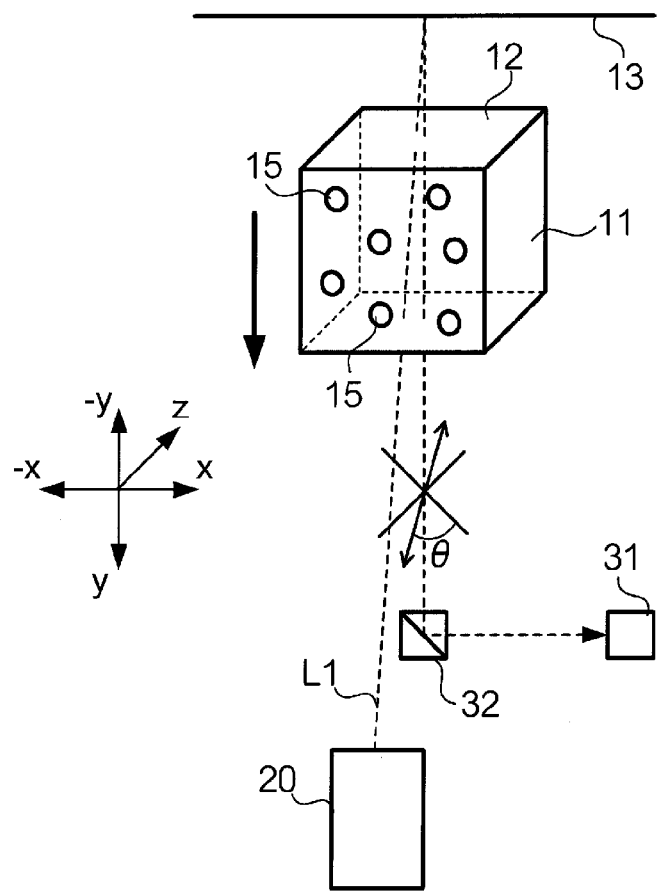
FIG. 8 is a view for explaining the principle of measuring a magnetic field from the back surface of the subject.

FIG. 8 is a view for explaining the principle of measuring a magnetic field from the back surface of the subject P. In FIG. 8, directions are indicated by using the three-dimensional coordinate system (left-hand system). Besides, in this drawing, for facilitating the explanation, only one of the plural cells 11 arranged on the back surface side of the subject P is shown.

The cell 11 arranged on the back surface side of the subject P includes the detection surface 12 parallel to an xz plane. The irradiation unit 20 irradiates the detection light L1 to a surface of the cell 11 opposite to the detection surface 12. The detection light L1 irradiated from the irradiation unit 20 is incident on this surface and passes through the cell 11. The detection light L1 passing through the cell 11 is reflected by the mirror 13, is incident on the detection surface 12 of the cell 11, and passes through the cell 11 in the y-axis direction. At this time, the polarization plane of the detection light L1 is rotated by the alkali metal atom 15 in the cell 11 by a rotation angle θ according to the intensity of the magnetic field in the y-axis direction. The detection light L1 passing through the cell 11 is guided to the detector 31 by the mirror 32. When receiving the detection light L1, the detector 31 detects the rotation angle θ of the polarization plane of the detection light L1. The rotation angle θ has a value corresponding to the intensity of the magnetic field in the y-axis direction in the cell 11. Accordingly, the magnetic field in the y-axis direction in the cell 11 can be measured by the detecting the rotation angle θ.

Since the distance from the heart H at the front surface of the subject P is small as compared to that at the left side surface or the back surface, the intensity of the magnetocardiogram generated from the body surface is high. Thus, even if the first cell 11a having sensitivity lower than that of the second cell 11b is used, the magnetic field can be measured. Then, the first cells 11a smaller than the second cells 11b are arranged on the front surface side of the subject P, and the first cells 11a are arranged so that the number thereof per unit area becomes larger. As stated above, the first cells 11a are arranged at a high density, so that the spatial resolution can be raised when the magnetic field is measured from the front surface of the subject P.

On the other hand, the distance from the heart H at the left side surface side and the back surface of the subject P is large as compared to that at the front surface, the intensity of the magnetocardiogram generated from the body surface is low. Thus, the second cells 11b larger than the first cells 11a are arranged on the left side surface side and the back surface side of the subject P so that a very weak magnetic field can be measured. As stated above, the second cell 11b is larger than the first cell 11a not only in the whole size but also in the size of the detection surface 12. Accordingly, the sensitivity when the magnetic field is measured from the side surface and the back surface of the subject P can be raised. That is, the measurement lower limit when the magnetic field is measured from the side surface and the back surface of the subject P can be reduced.

As stated above, the cells 11 are arranged on the front surface side, the side surface side and the back surface side of the subject P, so that the magnetic field can be measured not only from the front surface of the subject P but also from the side surface and the back surface. By this, the magnetic fields having the plural axial direction components can be measured.

When the magnetic field measuring apparatus 1 is used as a magnetocardiograph, the distribution of current flowing on the surface of the heart H is estimated based on the intensity of the measured magnetic field, and can be used for diagnosis. For example, a magnetic field distribution view is formed from the intensity of the measured magnetic field, and heart electromotive force is estimated by using the Biot-Savart law. At this time, since it is difficult to estimate the magnitude and distance of current flowing in a certain degree of volume from the measured magnetic field by an inverse problem or the like, in general, the optimum solution is obtained by using a minimum-norm method of estimating the position and magnitude of current from the waveform of a magnetic field distribution or curve fitting of waveform. However, for example, when two electric current dipoles have different positions and magnitudes, it is difficult to separate the respective electric current dipoles by merely measuring the magnetocardiogram from the front surface of the subject P.

Figure 9A:
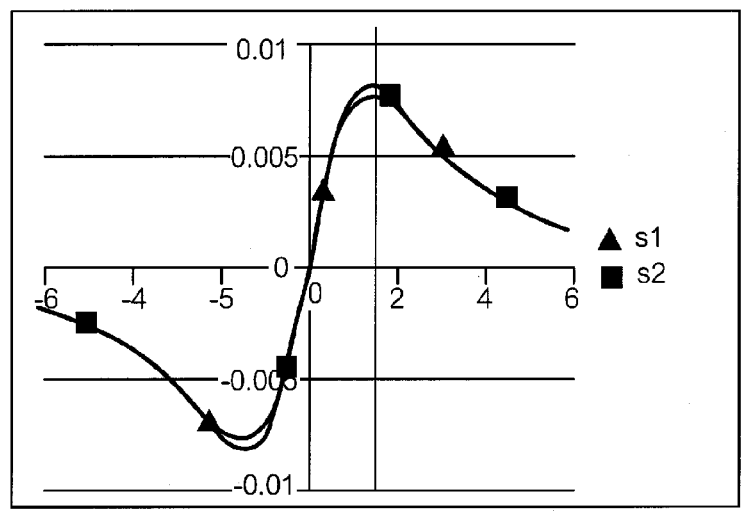
FIGS. 9A and 9B are views showing results of measurement of a magnetocardiogram.
Figure 9B:
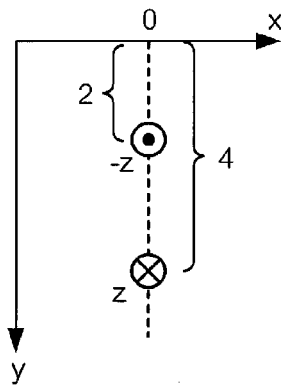
Figure 9B:
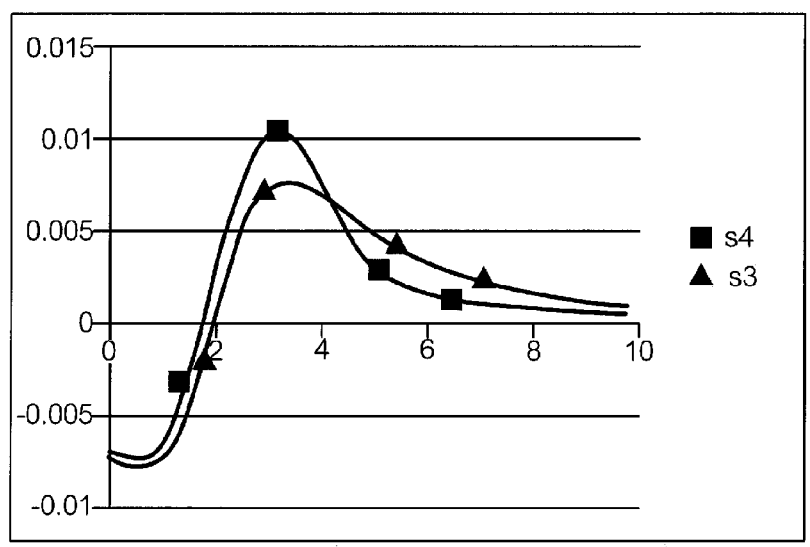

FIGS. 9A and 9B are views showing the results of magnetocardiogram measurement. The graph shown in FIG. 9A shows the results of magnetocardiogram measurement from the front surface of the subject P. In FIG. 9A, the horizontal axis indicates a position (in an arbitrary unit) in the x-axis direction, and the vertical axis indicates a measurement value (intensity of magnetic field) (in an arbitrary unit). The graph shown in FIG. 9B shows the results of magnetocardiogram measurement from the left side surface of the subject P. In FIG. 9B, the horizontal axis indicates a position (in an arbitrary unit) in the y-axis direction, and the vertical axis indicates a measurement value (intensity of magnetic field) (in an arbitrary unit).

For example, in the two-dimensional coordinate system shown in FIGS. 9A and 9B, it is assumed that a first current source exists at a position of (x, y)=(0, 2) (that is, the position where the distance in the y-axis direction is 2). The magnitude of a current outputted from the first current source is 1, and the direction of the current is the −z-axis direction (direction directed from the back to the front of the paper plane). If only the first current source exists, the measured value becomes a waveform s1 when the magnetocardiogram of the subject P is measured from the front surface. On the other hand, it is assumed that a second current source exists at a position of (x, y)=(0, 4) in the two-dimensional coordinate system shown in FIGS. 9A and 9B (that is, the position where the distance in the y-axis direction is 4) in addition to the first current source. The magnitude of a current outputted from the second current source is 0.3, and the direction of the current is the z-axis direction (direction directed from the front to the back of the paper plane). If the first current source and the second current source exist as stated above, the measured value becomes a waveform s2 when the magnetocardiogram of the subject P is measured from the front surface. Since the waveform s1 and the waveform s2 are similar to each other, it is difficult to determine the difference between them.

Then, attention is paid to results obtained by measuring the magnetocardiogram of the subject P from the left side surface. If only the first current source exists, the measurement value becomes a waveform s3 when the magnetocardiogram of the subject P is measured from the left side surface. On the other hand, if the first current source and the second current source exist, the measurement value becomes a waveform s4 when the magnetocardiogram of the subject P is measured from the left side surface. The waveform s2 and the waveform s4 are significantly different from each other. Thus, the first current source and the second current source can be easily separated.

As stated above, if the position of the electric current dipole (distance in the y-axis direction) can be estimated by measuring the magnetic field from not only the front of the subject P but also from the side surface or the back surface thereof, the problem becomes to solve only the magnitude of the current, and the accuracy of the estimation can be raised. As a result, with respect to the current flowing through the heart, a more accurate current distribution can be formed.

2. Modified Example

The invention is not limited to the foregoing embodiment, but can be variously modified. Hereinafter, some modified examples will be described. In the following modified examples, two or more modified examples may be combined and used.

(1) Modified Example 1

In the foregoing embodiment, although only the second cells 11b are arranged on the left side surface side and the back surface side of the subject P, the first cells 11a may be arranged also on the left side surface side or the back surface side. In this case, the first cells 11a may be arranged in an area close to the heart H of the subject P, and the second cells 11b may be arranged in an area far from the heart H. The area close the heart H is an area within a specified range from the heart H, and the area far from the heart H is the other area.

Figure 10:
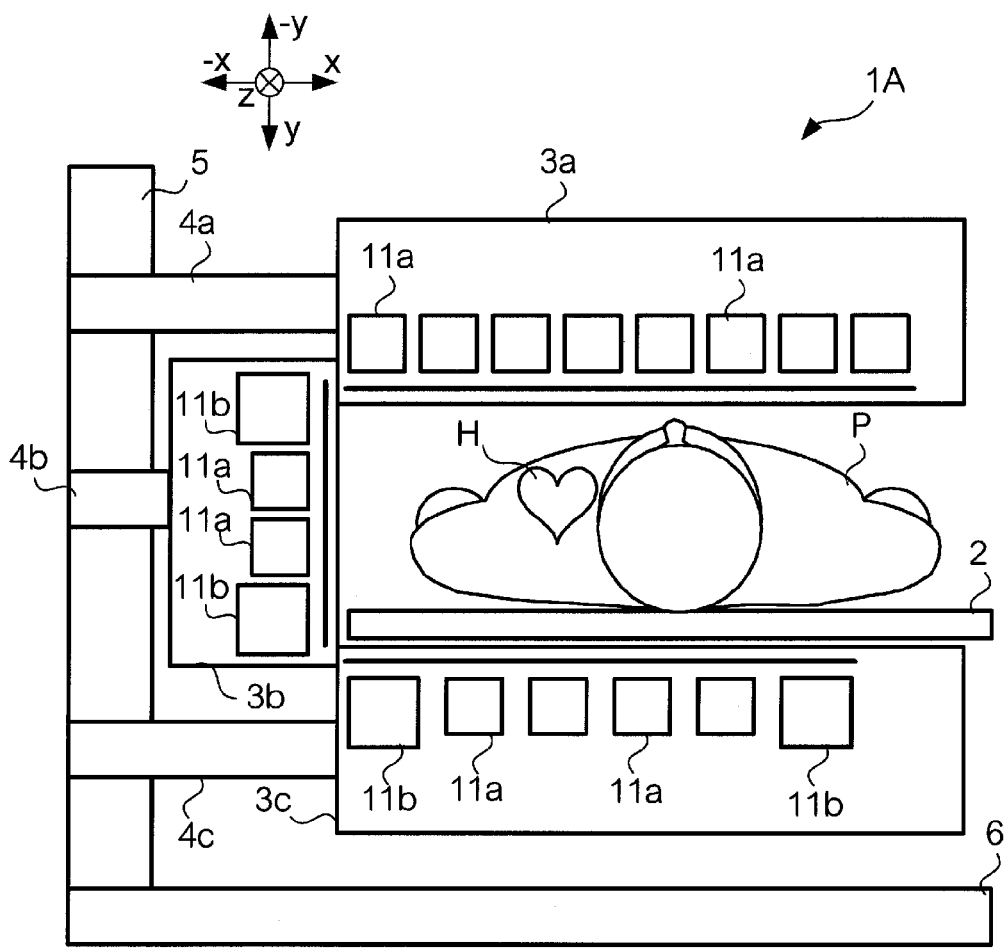
FIG. 10 is a view showing an example of an arrangement of cells of a modified example.

FIG. 10 is a view showing an example of arrangement of cells 11 in a magnetic field measuring apparatus 1A of this modified example. In this example of FIG. 10, the first cells 11a and the second cells 11b are arranged on the left side surface side of the subject P. The first cells 11a are arranged at the center portion close to the heart H of the subject P. On the other hand, the second cells 11b are arranged at the end portions far from the heart H of the subject P. Besides, the first cells 11a and the second cells 11b are arranged also on the back surface side of the subject P. The first cells 11a are arranged at the center portion close to the heart H of the subject P. On the other hand, the second cells 11b are arranged at the end portions far from the heart H of the subject P. By this, even when the magnetic field is measured from the left side surface or the back surface of the subject P, the spatial resolution can be raised in the area close to the heart H.

(2) Modified Example 2

In the foregoing embodiment, although only the first cells 11a are arranged on the front surface side of the subject P, and only the second cells 11b are arranged on the side surface side and the back surface side, cells 11 different in size may be mixedly arranged. In this case, the first cells 11a may be arranged in an area close to the heart H of the subject P, and the second cells 11b may be arranged in an area far from the heart H. The area close to the heart H is an area within a specified range from the heart H, and the area far from the heart H is the other area.

Figure 11:
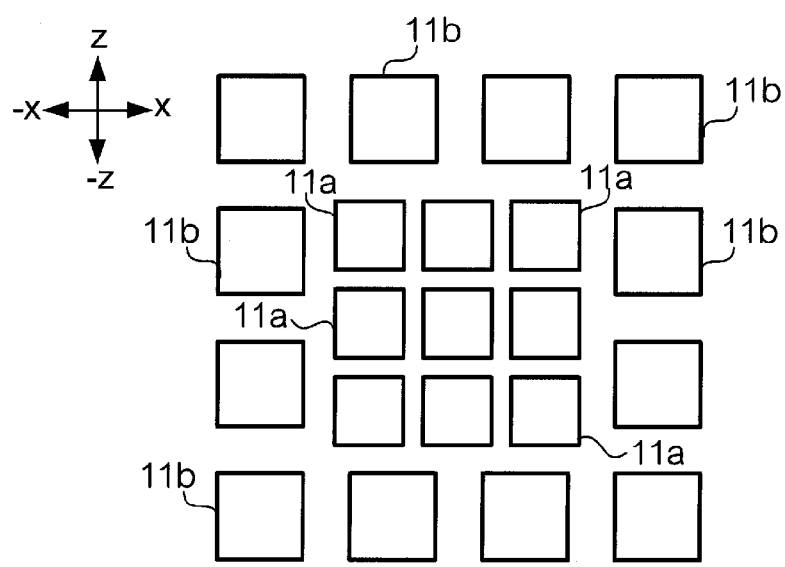
FIG. 11 is a view showing an example of an arrangement of cells of a modified example.

FIG. 11 is a view showing an example of arrangement of cells 11 of this modified example. In FIG. 11, the cells 11 arranged on the front surface side of the subject P are shown. The first cells 11a and the second cells 11b are arranged on the front surface side of the subject P. The first cells 11a are arranged at the center portion close to the heart H of the subject P. On the other hand, the second cells 11b are arranged at the end portions far from the heart H of the subject P. By this, the spatial resolution can be raised in the area close to the heart H of the subject P, and the sensitivity when the magnetic field is measured can be raised (measurement lower limit is reduced) in the area far from the heart H of the subject P.

(3) Modified Example 3

In the foregoing embodiment, although the plural cells 11 are two-dimensionally arranged in the matrix on the front surface side, the left side surface side and the back surface side of the subject P, the arrangement of the plural cells 11 is not limited to this.

Figure 12:
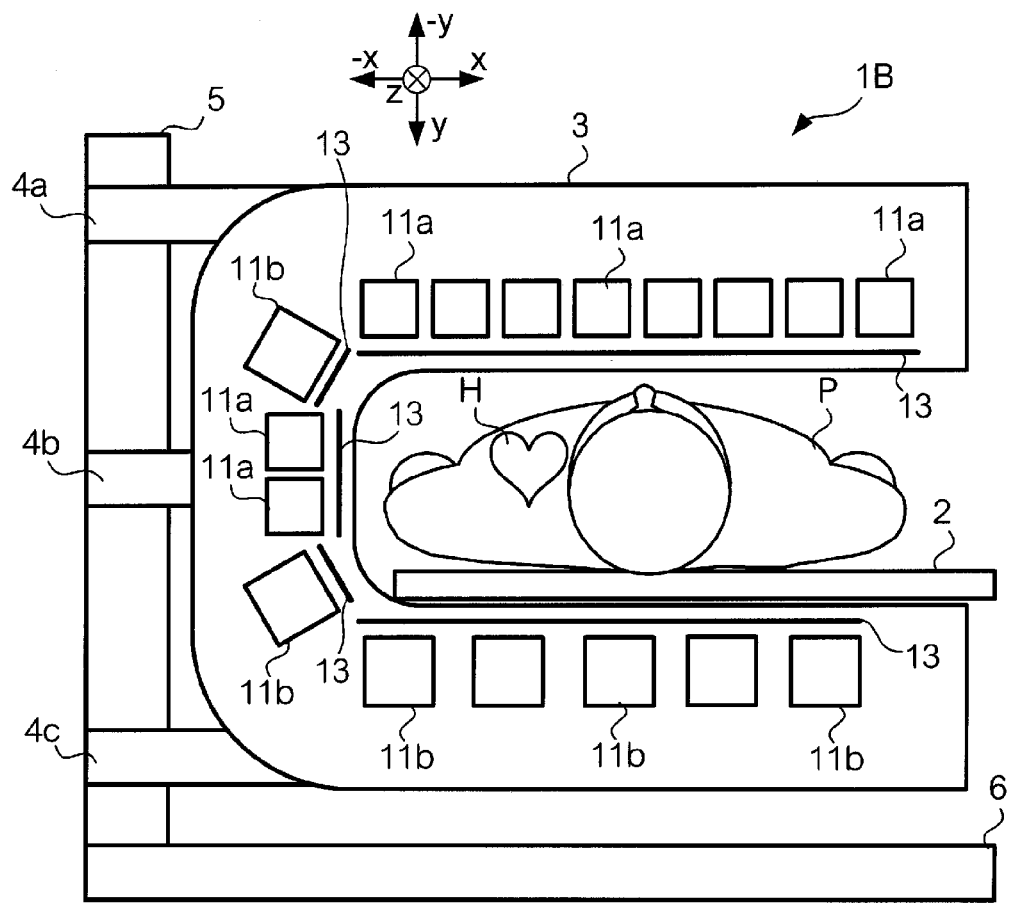
FIG. 12 is a view showing an example of an arrangement of cells of a modified example.

FIG. 12 is a view showing an example of arrangement of cells 11 of a magnetic field measuring apparatus 1B of this modified example. The side surface of the subject P has a rounded shape. Then, in the example of FIG. 12, the cells 11 on the left side surface side of the subject P are arranged to coincide with the roundness of the body of the subject P. Incidentally, in this case, instead of the housings 3a, 3b and 3c shown in FIG. 2, a housing 3 containing all the cells 11 included in the cell array 10 may be provided. As stated above, the cells 11 may be arranged along the shape of the body of the subject P. By this, the distance between the heart H and the cell 11 can be reduced. As a result, the sensitivity when the magnetic field is measured can be raised (measurement lower limit is reduced).

(4) Modified Example 4

The sizes of the cells 11 are not limited to two kinds of sizes. For example, cells 11 having three kinds of sizes may be used. In this case, for example, the smallest cells 11 are arranged in an area close to the heart H, the largest cells 11 are arranged in an area far from the heart H, and middle-sized cells 11 are arranged in an area between them. That is, the cells having the smallest detection surfaces 12 are arranged in the area within a specified range from the heart H, and the cells having larger detection surfaces 12 are arranged in the areas farther from the heart H. Besides, in this case, the cells 11 having the smaller detection surfaces 12 are arranged so that the number of the cells 11 per unit area becomes large.

(5) Modified Example 5

The number of the cells 11 is not limited to that explained in the embodiment. The number of the cells 11 may be determined based on, for example, the magnitude of a magnetic field of a measurement object or the position of a generation source thereof. The shape of the cell 11 is not limited to a cube. For example, the cell 11 may be rectangular or spherical. The arrangement of the cells 11 is not limited to the matrix form. For example, the plural cells 11 may be radially arranged. Besides, the shape of the cell 11 may be made a regular hexagonal column and the cells may be arranged in a honeycomb structure.

(6) Modified Example 6

In the foregoing embodiment, although the cells 11 are arranged on the front surface side, the left side surface side and the back surface side of the subject P, the cells 11 are not required to be arranged in all the areas. For example, the cells 11 may be arranged only on the front surface side and the back surface side of the subject P or on the front surface side and the left side surface side. In this case, the cells 11 are arranged to cover the heart H of the subject P from two directions. Alternatively, the cells 11 may be arranged on the right side surface side of the subject P in addition to the front surface side, the left side surface side and the back surface side. The right side surface side means an area positioned in the x-axis direction shown in FIG. 2 when viewed from the subject P. In this case, the cells 11 are arranged to cover the heart H of the subject P from the four directions.

(7) Modified Example 7

The magnetic field measured by the magnetic field measuring apparatus 1 is not limited to the magnetocardiogram. For example, a magnetic field (magnetoencephalogram) generated from a brain may be measured. In this case, the cells 11 may be arranged on the front surface side, the back surface side, the left side surface side, the right side surface side, and the overhead side of the subject P. The overhead side is an area above the head when the subject P stands. In this case, the cells 11 are arranged to cover the head of the subject P from the five directions.

(8) Modified Example 8

In the foregoing embodiment, the measurement of the magnetic field is performed from the plural directions. However, the measurement of the magnetic field may be performed from only one direction. For example, when the measurement of the magnetic field is performed only from the front surface of the subject P, the first cells 11a and the second cells 11b are arranged only on the front surface side of the subject P. In this case, as shown in FIG. 11, the first cells 11a may be arranged in an area close to the heart H of the subject P, and the second cells 11b may be arranged in the other area.

(9) Modified Example 9

The structure of the magnetic field measuring apparatus 1 is not limited to that shown in FIG. 2. For example, a chair may be used instead of the bed 2. The magnetic field measuring apparatus 1 has only to have such a structure that the cells 11 can be arranged in plural directions when viewed from the subject P.

(10) Modified Example 10

The magnetic field measuring apparatus 1 may measure a magnetic field by using a pump light L2 and a detection light L1. In this case, the magnetic field measuring apparatus 1 includes a pump light irradiation unit to irradiate the pump light L2. The pump light irradiation unit includes a light source, a polarizing part and a light distributor. The light source emits a laser light. The polarizing part polarizes the laser light emitted from the light source and generates the pump light L2 having a circularly-polarized component. The light distributor branches the pump light L2 generated by the polarizing part into lights the number of which is equal to the number of the cells 11 included in the cell array 10. The pump light L2, which is branched by the light distributor into the plural lights, is guided by, for example, an optical fiber and is irradiated to each of the cells 11 included in the cell array 10.

Figure 13:
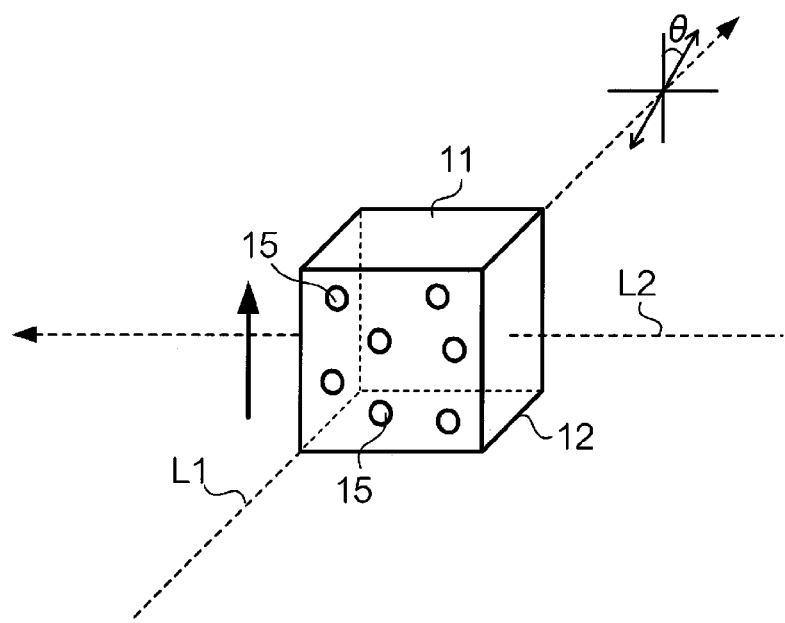
FIG. 13 is a view for explaining the measurement principle of a magnetic field of a modified example.

FIG. 13 is a view for explaining the measurement principle of magnetic field in this modified example. The pump light irradiation unit irradiates the pump light L2 to the cell 11 in a direction perpendicular to the detection light L1. When the pump light L2 is irradiated, the outermost electron of the alkali metal atom 15 in the cell 11 is excited, and spin polarization occurs. The spin-polarized alkali metal atom 15 performs a precession movement by the magnetic field. Although the spin polarization of the one alkali metal atom 15 is relaxed with the elapse of time, since the pump light L2 is a CW (Continuous Wave) light, the formation and relaxation of the spin polarization are repeated concurrently and continuously. As a result, when the whole group of atoms is considered, static spin polarization is formed. Next, the irradiation unit 20 irradiates the detection light L1 to the detection surface 12 of the cell 11. The detection light L1 passing through the cell 11 is received by the detector 31, and a rotation angle θ of the polarization plane thereof is detected. By this, the magnetic field can be measured.

(11) Modified Example 11

The magnetic field measuring apparatus 1 is not limited to the optical pumping type magnetic sensor. For example, the magnetic field measuring apparatus 1 may be a flux-gate magnetometer. The flux-gate magnetometer uses the magnetization saturation characteristic of high-permeability material and measures one directional component of the magnetic field. The principle of the flux-gate magnetometer is as described below. First, a primary coil and a secondary coil are wound around a magnetic core of ferromagnetic material such as permalloy. When a sine-wave current flows through the primary coil, an alternating current shifted from the sine wave arises in the secondary coil due to the saturation characteristic of the magnetic material. If an external magnetic field does not exist, the waveform of the secondary coil includes the fundamental wave and only odd-order harmonic waves. However, if an external magnetic field is superimposed, the waveform includes also even-order harmonic waves. Accordingly, when the amplitudes of harmonic components of the original sine wave are extracted, the intensity of the component of the external magnetic field in the direction of the magnetic core can be obtained.

Similarly to the optical pumping type magnetic sensor, when the flux-gate magnetometer is arranged in a magnetic field of a measurement object, the sensitivity is changed according to the size of a detection surface through which a magnetic flux passes. That is, the magnetic field measuring apparatus 1 may be any magnetic sensor that has such a characteristic that when the sensor is arranged in a magnetic field of a measurement object, the sensitivity is changed according to a detection surface through which a magnetic flux passes. Besides, the magnetic field measuring apparatus 1 preferably has sufficient sensitivity to measure a very weak magnetic field such as a magnetocardiogram, so that the magnetic field measuring apparatus can be used as a magnetocardiograph. Further, the magnetic field measuring apparatus 1 preferably measures the magnetic field by a method having the degree of freedom with respect to the arrangement of respective parts, so that the magnetic field can be measured not only from the front surface of the subject P but also from the side surface or the back surface.

(12) Modified Example 12

In the foregoing embodiment, although the mirror 13 is provided between each of the cells 11 and the subject P in the magnetic field measuring apparatus 1, the mirror 13 may not be provided. In this case, the detection light passing through the cell 11 is guided to the detector by using, for example, a waveguide. Alternatively, when the influence of the detector on magnetic properties is small, the detector may be provided between the cell 11 and the subject P.

The entire disclosure of Japanese Patent Application No. 2011-272345, filed Dec. 13, 2011 is expressly incorporated reference herein.

What is claimed is:

1. A magnetic field measuring apparatus comprising:
   a housing that has a first surface and a second surface orthogonal to the first surface;
   a first cell array that includes a plurality of first cells being arranged in a first matrix form;
   a second cell array that includes a plurality of second cells being arranged in a second matrix form, wherein the first cells and the second cells are different in size;
   a substance that is enclosed inside each of the plurality of first cells and each of the plurality of second cells, wherein the substance rotates a polarization plane of a given light according to an intensity of a magnetic field;
   an irradiator to irradiate a light to the detection surface of each of the first cells and each of the second cells; and
   a detector to detect a rotation angle of the polarization plane of the light irradiated by the irradiator and passing through each of the first cells and each of the second cells, wherein:
   the first cell array is arranged along the first surface and the second cell array is arranged along the second surface,
   the first cells of the first cell array are arranged at a higher density in the first matrix form than the second cells of the second cell array are arranged in the second matrix form, and
   a distance between the first cell array and a measurement object is smaller than a distance between the second cell array and the measurement object.

2. A cell array for a magnetic field measuring apparatus, the cell array comprising:
   a housing that has a first surface and a second surface orthogonal to the first surface;
   a plurality of first cells arranged in a first matrix form;
   a plurality of second cells arranged in a second matrix form, wherein the first cells are a different size than the second cells; and
   a substance that is enclosed inside each of the plurality of first cells and each of the plurality of second cells, wherein the substance rotates a polarization plane of a given light according to an intensity of a magnetic field, wherein
   the first cells are arranged along the first surface and the second cells are arranged along the second surface,
   the first cells are arranged at a higher density in the first matrix form than the second cells are arranged in the second matrix form, and
   a distance between a given first cell from among the first cells and a measurement object is smaller than a distance between a given second cell from among the second cells and the measurement object.

3. The magnetic field measuring apparatus according to claim 1, wherein the first cells are smaller in size than the second cells.

4. The magnetic field measuring apparatus according to claim 1, wherein the irradiator irradiates light in a first direction toward the first cell array and irradiates light in a second direction different from the first direction toward the second cell array.

5. The magnetic field measuring apparatus according to claim 1, wherein the irradiator irradiates light in a first direction toward the first cell array and irradiates light in a second direction toward the second cell array, the second direction is parallel to and in an opposite direction of the first direction.

6. A magnetic field measuring apparatus for measuring a magnetic field of a measurement object, the magnetic field measuring apparatus comprising:
   a housing that has a first surface and a second surface orthogonal to the first surface;
   a cell array that includes a plurality of first cells and a plurality of second cells, wherein the plurality of first cells are arranged in a first matrix form, the plurality of second cells are arranged outside of the first matrix form, and the first cells and the second cells are different in size;
   a substance that is enclosed inside each of the plurality of first cells and each of the plurality of second cells, wherein the substance rotates a polarization plane of a given light according to an intensity of the magnetic field;

an irradiator to irradiate a light to the detection surface of each the first cells and each of the second cells; and a detector to detect a rotation angle of the polarization plane of the light irradiated by the irradiator and passing through each of the first cells and each of the second cells, wherein:

the first cells are arranged along the first surface and the second cells are arranged along the second surface, the first cells are arranged at a higher density in the first matrix form than the second cells are arranged in a second matrix form, and a distance between a given first cell from among the first cells and a measurement object is smaller than a distance between a given second cell from among the second cells and the measurement object.

\* \* \* \* \*